US005565343A

United States Patent [19]

Klages et al.

[11] Patent Number: 5,565,343
[45] Date of Patent: Oct. 15, 1996

[54] PROCESS FOR THE PRODUCTION OF DULCITOL FROM LACTOSE

[75] Inventors: Uwe Klages; Alfred Weber; Mario Kennecke, all of Berlin, Germany

[73] Assignee: Schering Aktiengesellschaft, Berlin, Germany

[21] Appl. No.: 297,438

[22] Filed: Aug. 29, 1994

Related U.S. Application Data

[63] Continuation of Ser. No. 924,017, filed as PCT/DE92/00008 Jan. 3, 1992, abandoned.

[30] Foreign Application Priority Data

Jan. 24, 1991 [DE] Germany ............................ 41 02 243.2

[51] Int. Cl.$^6$ ................. C12P 19/02; C12P 1/02; C12N 1/16
[52] U.S. Cl. .................. 435/105; 435/171; 435/255.1
[58] Field of Search ........................ 435/119, 255, 435/171, 105, 255.1

[56] References Cited

PUBLICATIONS

Chemical Dictionary, Grant et al, McGraw–Hill Book Company; New York, 1987, pp. 149–176.

Stryer, *Biochemistry* (3rd Ed.), W. H. Freeman and Company: New York, (1988), 358–359.

Stanbury et al, *Principles of Fermentation Technology*, Pergamon Press: New York, (1984), 21–24.

"Genetic and Biochemical Characterization of the Galactose Gene Cluster.." J. of Bacteriology, May 1984, vol. 158, No. 2., pp. 705–712.

"Strain selection in Kluyveromyces marxianus var. lactis for galactose production", M. Helene Marin et al., J. Basic Microbiol. 27 (1987) pp. 505–510.

"Utilization of Carbon Sources During Penicillin Biosynthesis", V. Matelova, *Folia microbiologica*, vol. 21 (3), 1976, pp. 161–256.

*Primary Examiner*—Michael G. Wityshyn
*Assistant Examiner*—Francisco C. Prats
*Attorney, Agent, or Firm*—Millen, White, Zelano, & Branigan, P.C.

[57] ABSTRACT

A process for the production of dulcitol by fermentative reaction of lactose by galactokinase-negative mutants of genus Kluyveromyces is described, which is characterized in that 5 g to 25 g of glucose is added to the fermentation culture after substantial hydrolysis of the lactose per liter or the fermentation is performed under the conditions of the resting-cell process.

13 Claims, No Drawings

PROCESS FOR THE PRODUCTION OF DULCITOL FROM LACTOSE

This application is a continuation of application Ser. No. 07/924,017, filed as PCT/DE92/00008 Jan. 3, 1992, now abandoned.

The invention relates to a process for the production of dulcitol by fermentative reaction of lactose by galactokinase-negative mutants of genus Kluyveromyces.

It is known that galactokinase-negative mutants of genus Kluyveromyces have the capability to cleave the disaccharide lactose in glucose and galactose, to metabolize the glucose and not to attack the galactose. (Michael I. Riley et al., J. Bacteriol. 158, 1984, 705–712 and Pierre Galzy et al., DE-A 24 34 874). Further, it is known that there are also mutants which are able to hydrogenate the galactose formed in this reaction to dulcitol with a yield up to about 50% (M.-Héléne Marin et al., J. Basic Microbiol. 27, 1987, 505–510).

If it is desired to produce dulcitol from lactose in this previously known way, it is necessary to convert the latter first with a galactokinase-negative mutant of genus Kluyveromyces, to isolate the formed galactose, or the mixture of galactose and dulcitol and then to convert to dulcitol by hydrogenation (Beilstein, 4th edition, 3rd supplementary work, first volume, 2405–2406). But this process is essentially more expensive than recovering dulcitol from Madagascar manna (Melampyrum nemorosum) (Roempps Chemie-Lexikon, 8th edition, Franck'sche Verlagshandlung, Stuttgart, p. 1027).

The process according to the invention makes it possible to convert lactose by fermentative reaction with galactokinase-negative mutants of genus Kluyveromyces to dulcitol in high yields. The obtained dulcitol contains practically no or only small amounts of galactose (normally less than 5%) and can consequently be purified by simple recrystallization—for example from aqueous ethanol.

The process according to the invention is characterized in that in the fermentative reaction of lactose with galactokinase-negative mutants of genus Kluyveromyces, a) 5 g to 25 g of glucose is added to the fermentation culture after substantial hydrolysis of the lactose per liter or b) the fermentation is performed under the conditions of the resting-cell process.

To perform the process according to the invention, the mutants of Kluyveromyces can be used which are described in the already mentioned publications of Riley et al., Galzy et al. or Marin et al.

Since not all mutants which are mentioned in these publications are freely available to experts, separate mutation tests were performed under the conditions described by Marin et al. and a mutant with internal designation 144 EH was obtained, which in all essential features taxonomically has the properties of Kluyveromyces marxianus var. lactis (J. Lodder "The Yeasts," North-Holland Publ. Comp., Amsterdam 1971, 349–352). This mutant was deposited in the Deutsche Sammlung von Mikroorganismen und Zellkulturen GmbH [German Collection of Microorganisms and Cell Cultures GmbH], D-3300 Brunswick under the DSM no. 6119, it is freely available to experts and has proved especially suitable for performing the process according to the invention.

The process according to the invention is performed under the conditions which are also used in the known microbiological conversions of substrates with yeast cultures.

Under the cultivation conditions usually used for yeast cultures, in particular Kluyveromyces cultures, preliminary cultures are cultivated in a suitable nutrient medium with aeration and stirring.

To perform process variant a, an aliquot part of this preliminary culture is converted to a fermentation medium, which contains 10 g to 50 g (in particular 20 g to 30 g) of lactose besides the usual nutrient media per liter of culture. Then, it is fermented with stirring and aeration at a temperature of 25° C. to 30° C. and a pH of 4 to 6, until about at least 95% of the lactose is hydrolytically cleaved, 0.25 g to 1 g (preferably 0.4 g to 0.6 g) of glucose is added to the fermentation culture per g of lactose and further fermented until the reaction dies down.

The optimum lactose concentration and glucose concentration, the optimum time of the glucose addition and the optimum fermentation time are dependent on the type of the Kluyveromyces mutant used and the fermentation conditions. These values, as is generally necessary in the individual case in microbiological substrate conversions, have to be determined by preliminary tests as they are familiar to one skilled in the art.

To determine the course of fermentation, samples can be taken from the culture in time intervals and their content of lactose, galactose, glucose and dulcitol in the samples can be determined in the usual way—for example, by thin-layer chromatography.

To perform the process variant, a Kluyveromyces culture is cultivated under the conditions of variant a, but without adding lactose. After a growth phase of about 24 to 48 hours, the cell mass is separated by filtration or centrifugation, washed and resuspended in a 0.5 to 10 (preferably 1 to 5) % by weight aqueous lactose solution containing optionally isotonizing additives and buffer substances, so that the cell density in this suspension is 2 to 5 times greater than in the fermentation culture. Then, it is fermented with stirring and aeration until the reaction dies down.

Also, in this case, it is necessary to determine the optimum reaction parameters by preliminary tests.

After the reaction has been completed, the dulcitol can be isolated from the fermentation batches obtained according to variant a or b in a simple way. This can happen, for example, by the batches being filtered or centrifuged, the obtained solutions being freed from inorganic salts, concentrated by evaporation, and the dulcitol being brought to crystallization by adding suitable solvents such as ethanol.

The thus produced dulcitol can—optionally after recrystallization—be used, for example, as sugar-free sweetener.

The following embodiments are used to explain the process according to the invention in more detail.

EMBODIMENTS

EXAMPLE 1

A 2 l Erlenmeyer flask with 1 l of a sterile nutrient solution containing 5 g/l of $(NH_4)_2SO_4$ 1 g/l of $KH_2PO_4$ 0.5 g/l of $MgSO_4 \cdot 7H_2O$ 0.1 g/l of NaCl 0.1 g/l of $CaCl_2$ 400 micrograms/l of nicotinic acid 2 micrograms/l of biotin 400 micrograms/l of thiamine hydrochloride 10 mg/l of adenine 5 g/l of lactose —adjusted to pH 4 — is inoculated with an inoculating loop with cells of Kluyveromyces marxianus DSM 6119 and shaken for 36 hours at 30° C. and 190 rpm.

A 50 l fermenter with 40 l of a sterile nutrient solution of the same composition as the preliminary culture is inoculated with 1 l of preliminary culture. The batch is heated moderately to 30° C. and stirred for 24 hours with 100 rpm and aerated with 1 $m^3$ of air per hour.

A 50 l fermenter with 32 l of a sterile nutrient solution of the same composition as the preliminary fermenter, but with 20 g/l of lactose and adjusted to pH 5, is inoculated with 4 l of the preliminary fermenter culture and stirred at 30° C. with 100 rpm and aerated with 1 $m^3$ of air per hour.

The pH is adjusted so that it does not drop under pH 5. After 48 hours, a sterile solution of 400 g of glucose in 4 l of water is added.

After 96 hours, the batch is mixed with 100 g each of activated carbon and perlite and filtered. The cell-free culture broth is desalted on an electrodialysis device to a conductivity of 0.2 mS. The solution is concentrated in a vacuum to about 1 l and mixed with the same volume of ethanol. 374 g of dulcitol is obtained as crystallizate.

EXAMPLE 2

A 500 ml Erlenmeyer flask with 100 ml of a sterile nutrient solution containing 3 g/l of yeast extract 3 g/l of malt extract 5 g/l of peptone 10 g/l of lactose is inoculated with an inoculating loop with cells of Kluyveromyces marxianus DSM 6119 and Shaken for 24 hours at 30° C. and 180 rpm.

The cells are separated by centrifuging the medium, washed once with 0.9% common salt solution and resuspended in 20 ml of deionized water containing 0.5 g/l of $MgCl_2$ and 10 g/l of lactose and adjusted to pH 4.5.

The batch is shaken at 30° C. with 180 rpm. After 24 hours, the cells are centrifuged off. It is determined by TLC analysis that 5 g/l of dulcitol is contained in the supernatant.

Reference example

The cultivation of the preliminary culture and the preliminary fermenter takes place as described in example 1.

A 50 l fermenter with 36 l of a sterile nutrient solution of the same composition as the preliminary fermenter, but with 20 g/l of lactose and adjusted to pH 5, is inoculated with 4 l of the preliminary fermenter culture and stirred at 30° C. with 100 rpm and aerated with 1 $m^3$ of air per hour. The pH is adjusted so that it does not fall under pH 5.

After 72 hours, the batch is mixed with 100 g each of activated carbon and perlite and filtered. The cell-free culture broth is desalted on an electrodialysis device to a conductivity of 0.2 mS. The solution is concentrated in a vacuum to about 1 l and mixed with the same volume of ethanol. 160 g of galactose and 212 g of dulcitol are obtained as crystallizate.

We claim:

1. A process for the production of dulcitol by a galactokinase-negative mutant *Kluyveromyces marxianus* var. *lactis* DSM 6119 comprising, growing the galactokinase-negative mutant to a resting-cell phase; and culturing said galactokinase-negative mutant under resting-cell conditions in a fermentation medium containing lactose wherein dulcitol is produced, wherein the resting-cell conditions comprise culturing said galactokinase-negative mutant at a cell concentration 2 to 5 times greater than the cell concentration at which the resting-cell phase was reached; and recovering said dulcitol.

2. The process according to claim 1, wherein 10 gm to 50 gm of lactose is present per liter of fermentation medium.

3. The process according to claim 1, wherein the resting-cell phase is attained by growing said galactokinase-negative mutant for about 24 to 48 hours.

4. A process according to claim 1, wherein the process further comprises recovering dulcitol by crystallization.

5. A process according to claim 1, wherein the recovered dulcitol comprises 5% or less of galactose.

6. A process for the production of dulcitol by a galactokinase-negative mutant *Kluyveromyces marxianus* var. *lactis* DSM 6119 comprising, culturing said galactokinase-negative mutant in a fermentation medium containing lactose, wherein said lactose is fermented by said mutant;

adding 5 gm to 25 gm of glucose per liter to said fermentation medium at a time effective to enhance the production of dulcitol; and recovering said dulcitol.

7. A process according to claim 6, wherein the process further comprises recovering dulcitol by crystallization.

8. A process according to claim 6, wherein the recovered dulcitol comprises 5% or less of galactose.

9. A process for the production of dulcitol by a galactokinase-negative mutant *Kluyveromyces marxianus* var. *lactis* DSM 6119, comprising:

culturing said galactokinase-negative mutant in a fermentation medium containing lactose, wherein said lactose is fermented by said mutant;

adding glucose to said fermentation medium after 95% of the lactose is hydrolytically cleaved;

further culturing said mutant, wherein dulcitol is produced by said mutant; and recovering said dulcitiol.

10. The process according to claim 9, wherein said fermentation medium contains 10 gm to 50 gm per liter of lactose.

11. A process according to claim 9, wherein about 5 to about 25 grams/liter of glucose is added to said fermentation medium after 95% of the lactose is hydrolytically cleaved.

12. A process according to claim 9, wherein the process further comprises recovering dulcitol by crystallization.

13. A process according to claim 12, wherein the recovered dulcitol comprises 5% or less of galactose.

* * * * *